United States Patent [19]

Saito et al.

[11] Patent Number: 4,963,288

[45] Date of Patent: Oct. 16, 1990

[54] FLUOROALKOXYDIPHENYL PYRIMIDINE, LIQUID CRYSTAL COMPOSITION AND ELECTRO-OPTIC ELEMENT

[75] Inventors: Shinichi Saito, Ichihara; Kazutoshi Miyazawa, Yokohama; Kouji Ohno, Ichihara; Hiromichi Inoue, Yokohama, all of Japan

[73] Assignee: Chisso Corporation, Osaka, Japan

[21] Appl. No.: 326,033

[22] Filed: Mar. 20, 1989

[30] Foreign Application Priority Data

Mar. 28, 1988 [JP] Japan .................................. 63-71891

[51] Int. Cl.$^5$ ..................... C09K 19/34; C07D 239/02
[52] U.S. Cl. .......................... 252/299.61; 252/299.01; 544/335; 350/350 R; 350/350 S
[58] Field of Search ...................... 252/299.61, 299.01; 350/350 R, 350 S; 544/335

[56] References Cited

U.S. PATENT DOCUMENTS

| | | | |
|---|---|---|---|
| 4,309,539 | 1/1982 | Boller et al. | 252/299.61 |
| 4,725,688 | 2/1988 | Taguchi et al. | 252/299.61 |
| 4,764,636 | 8/1988 | Sasaki et al. | 252/299.61 |
| 4,820,839 | 4/1989 | Krause et al. | 252/299.61 |
| 4,834,904 | 5/1989 | Krause et al. | 252/255.61 |

FOREIGN PATENT DOCUMENTS

| | | | |
|---|---|---|---|
| 225195 | 6/1987 | European Pat. Off. | 252/299.61 |
| 313284 | 4/1989 | European Pat. Off. | 252/299.61 |
| 61-215373 | 9/1986 | Japan | 252/299.61 |
| 61-215374 | 9/1986 | Japan | 252/299.61 |
| 61-240386 | 10/1986 | Japan | 252/299.61 |
| 63-22042 | 1/1988 | Japan | 252/299.61 |
| 63-183983 | 7/1988 | Japan | 252/299.61 |
| 63-196571 | 8/1988 | Japan | 252/255.61 |
| 2201415 | 9/1988 | United Kingdom | 252/299.61 |

*Primary Examiner*—Robert L. Stoll
*Assistant Examiner*—Cynthia Harris
*Attorney, Agent, or Firm*—Wenderoth, Lind & Ponack

[57] ABSTRACT

New fluoroalkoxydiphenyl pyrimidines which are organic compounds having optically active groups, liquid crystal compositions containing the said compounds and electro-optic elements using the said compositions are provided.

The compounds have the following general formula:

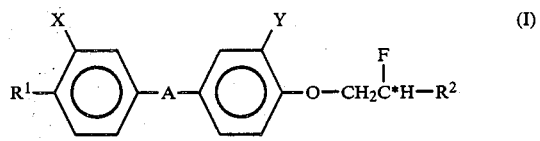

wherein $R^1$ is an alkyl or alkoxy group having 1-20 carbon atoms, a halogen atom or a cyano group, $R^2$ is a straight-chain or branched chain alkyl group having 1-15 carbon atoms, —A— is a group of

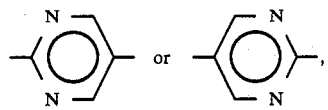

X and Y independently indicate a hydrogen atom, a halogen atom or a cyano group, and * indicates that its carbon atom is an asymmetric carbon atom.

5 Claims, No Drawings

FLUOROALKOXYDIPHENYL PYRIMIDINE, LIQUID CRYSTAL COMPOSITION AND ELECTRO-OPTIC ELEMENT

BACKGROUND OF THE INVENTION

The present invention relates to new optically active liquid crystal compounds, and liquid crystal compositions containing the said compounds, more particularly, the present invention relates to fluoroalkoxydiphenyl pyrimidines which are compounds having optically active groups, liquid crystal compositions containing the said compounds and electrooptic elements using the said compositions.

Liquid crystal display elements are widely used as various display elements, such as watches, electronic calculators, television sets, computer ends, etc., because these elements have excellent characters, such as operativity at low voltage, minimized consumption of electric power, obtainability of thin display elements and so on.

At present, display elements of a twisted nematic (TN) type are widely used as liquid crystal display elements. However, the response of the display element is slower than that of a display element of light emitting type such as an electroluminescent display, a plasma display, and the like. Although improvement of the response time of the liquid crystal display has been tried in many ways, it shows no sign of marked improvement.

However, a new display method using a ferroelectric liquid crystal that has been studied has a hope for the improvement of the response speed. (Clark et al, Appl. Phys. Lett. 36, 898 (1980)). This method utilizes a ferroelectric chiral smectic C phase (abbreviated as $S_C^*$ phase hereinafter) or other smectic phase such as a chiral smectic F, G, H or I phase and the like. This method is realizes a quick response time less than 1/100 to 1/1000 of that of the TN display method and a memory effect of bistability. It is expected to have wide application in a large sized television set of dynamic picture display, a high-speed light shutter, and the like.

However, in spite of these excellent characteristics, already-known compounds do not show a very quick response. The reason is that a compound having a high value of spontaneous polarization in the ferroelectric liquid crystal phase is unknown. The spontaneous polarization is proportional to the response speed. It is known that the high value of spontaneous polarization is important to obtain the quick response. Compounds having a high value of spontaneous polarization have not been found.

Hitherto, as ferroelectric liquid crystal compounds having a central group represented by the following formula:

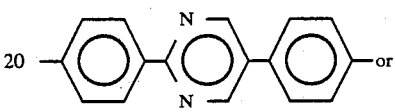

or

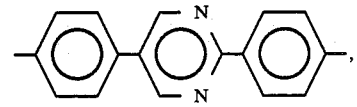

the following types are reported.

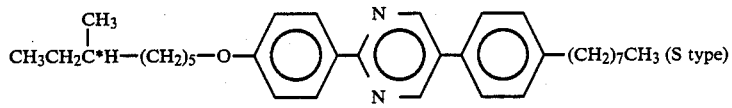

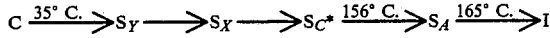

wherein $S_Y$ and $S_X$ are described as other smectic phases in Japanese Unexamined Publication No. 61-215373/1986.

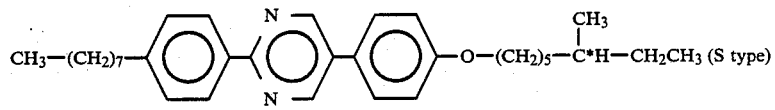

wherein $S_Y$ and $S_X$ are described as other smectic phases in Japanese Unexamined Publication No. 61-215373/1986.

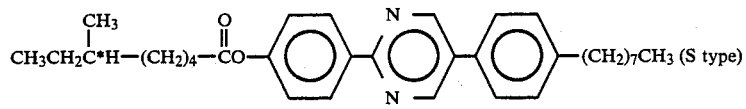

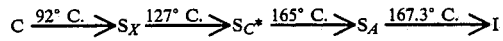

wherein $S_X$ is described as another smectic phase in Japanese Unexamined Publication No. 61-215374/1986.

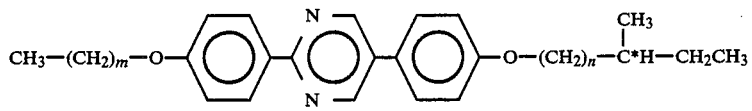

wherein when m is 1, n is 5 and when m is 6, n is 1, etc., in Lecture Collection of the thirteenth meeting of liquid crystal discussion 1Z03, page 46.

Furthermore, the following compounds are described in the specification which was filed by the inventors of the present invention. (Japanese Patent Application No. 62-262819/1987).

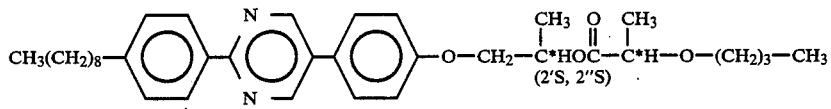

m.p. 98° C.

In the compounds described in the above Japanese Unexamined Publication Nos. 61-215373 and 61-215374/1986, and Lecture Collection of the thirteenth meeting of liquid crystal discussion 1Z03, the spontaneous polarization ($P_S$) which is an important physical property value of ferroelectric liquid crystals is very small. Moreover, the compounds described in the above Japanese Patent Application No. 62-262819 are difficult to show liquid crystal phases.

SUMMARY OF THE INVENTION

An object of the present invention is to provide optically active compounds having characteristics suited for the said display method which is still being researched, especially having enough spontaneous polarization to realize a quick response.

The present invention resides in a compound represented by the following general formula:

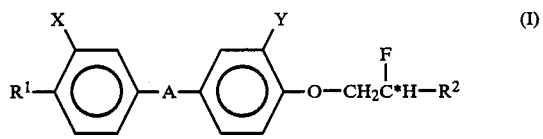

wherein $R^1$ is an alkyl or alkoxy group having 1-20 carbon atoms, a halogen atom or a cyano group, $R^2$ is a straight-chain or branched chain alkyl group having 1-15 carbon atoms, —A— is a group of

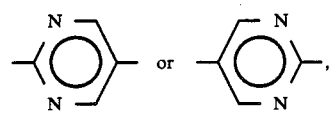

X and Y independently indicate a hydrogen atom, a halogen atom or a cyano group, and * indicates that its carbon atom is an asymmetric carbon atom.

The present invention also resides in a liquid crystal composition containing at least one of the above compounds.

DETAILED DESCRIPTION OF THE INVENTION $R^1$ is preferably an alkyl or alkoxy group having 3-16 carbon atoms, more preferably an alkyl or alkoxy group having 4-12 carbon atoms. $R^2$ is preferably an alkyl group having 1-10 carbon atoms and when the alkyl group is a branched chain group and an optically active group can be present, $R^2$ can be an optically active group. The preferable examples of $R^2$ are selected from the group of methyl, ethyl, propyl, butyl, pentyl, hexyl, heptyl, octyl, nonyl, decyl, isopropyl, sec-butyl, isobutyl and the like. X and Y are most preferably a combination of a hydrogen atom and a hydrogen atom, and then preferably a hydrogen atom and a fluorine atom, or a fluorine atom and a hydrogen atom.

Embodiments of the compounds of the present invention represented by the general formula (I) are as follows, without limiting the invention thereto.

No. 1. 2-(4'-Butylphenyl)-5-4'-(2''-fluoropropoxy)phenyl-pyrimidine

No. 2. 2-(4'-Pentylphenyl)-5-4'-(2''-fluoropropoxy)phenyl-pyrimidine

No. 3. 2-(4'-Hexylphenyl)-5-4'-(2''-fluoropropoxy)phenyl-pyrimidine

No. 4. 2-(4'-Heptylphenyl)-5-4'-(2''-fluoropropoxy)phenyl-pyrimidine

No. 5. 2-(4'-Octylphenyl)-5-4'-(2''-fluoropropoxy)phenyl-pyrimidine

No. 6. 2-(4'-Nonylphenyl)-5-4'-(2''-fluoropropoxy)phenyl-pyrimidine

No. 7. 2-(4'-Decylphenyl)-5-4'-(2''-fluoropropoxy)phenyl-pyrimidine

No. 8. 2-(4'-Undecylphenyl)-5-4'-(2''-fluoropropoxy)-phenyl-pyrimidine

No. 9. 2-(4'-Dodecylphenyl)-5-4'-(2''-fluoropropoxy)-phenyl-pyrimidine

No. 10. 2-(4'-Butylphenyl)-5-4'-(2''-fluorobutoxy)phenyl-pyrimidine

No. 11. 2-(4'-Pentylphenyl)-5-4'-(2''-fluorobutoxy)phenyl-pyrimidine

No. 12. 2-(4'-Hexylphenyl)-5-4'-(2''-fluorobutoxy)phenyl-pyrimidine

No. 13. 2-(4'-Heptylphenyl)-5-4'-(2''-fluorobutoxy)phenyl-pyrimidine

No. 14. 2-(4'-Octylphenyl)-5-4'-(2''-fluorobutoxy)phenyl-pyrimidine

No. 15. 2-(4'-Nonylphenyl)-5-4'-(2''-fluorobutoxy)phenyl-pyrimidine

No. 16. 2-(4'-Decylphenyl)-5-4'-(2''-fluorobutoxy)phenyl-pyrimidine

No. 17. 2-(4'-Undecylphenyl)-5-4'-(2"-fluorobutoxy)-phenyl-pyrimidine
No. 18. 2-(4'-Dodecylphenyl)-5-4'-(2"-fluorobutoxy)-phenyl-pyrimidine
No. 19. 2-(4'-Butylphenyl)-5-4'-(2"-fluoropentoxy)phenyl-pyrimidine
No. 20. 2-(4'-Pentylphenyl)-5-4'-(2"-fluoropentoxy)phenyl-pyrimidine
No. 21. 2-(4'-Hexylphenyl)-5-4'-(2"-fluoropentoxy)phenyl-pyrimidine
No. 22. 2-(4'-Heptylphenyl)-5-4'-(2"-fluoropentoxy)-phenyl-pyrimidine
No. 23. 2-(4'-Octylphenyl)-5-4'-(2"-fluoropentoxy)phenyl-pyrimidine
No. 24. 2-(4'-Nonylphenyl)-5-4'-(2"-fluoropentoxy)phenyl-pyrimidine
No. 25. 2-(4'-Decylphenyl)-5-4'-(2"-fluoropentoxy)phenyl-pyrimidine
No. 26. 2-(4'-Undecylphenyl)-5-4'-(2"-fluoropentoxy)-phenyl-pyrimidine
No. 27. 2-(4'-Dodecylphenyl)-5-4'-(2"-fluoropentoxy)-phenyl-pyrimidine
No. 28. 2-(4'-Butylphenyl)-5-4'-(2"-fluorohexyloxy)-phenyl-pyrimidine
No. 29. 2-(4'-Pentylphenyl)-5-4'-(2"-fluorohexyloxy)-phenyl-pyrimidine
No. 30. 2-(4'-Hexylphenyl)-5-4'-(2"-fluorohexyloxy)-phenyl-pyrimidine
No. 31. 2-(4'-Heptylphenyl)-5-4'-(2"-fluorohexyloxy)-phenyl-pyrimidine
No. 32. 2-(4'-Octylphenyl)-5-4'-(2"-fluorohexyloxy)-phenyl-pyrimidine
No. 33. 2-(4'-Nonylphenyl)-5-4'-(2"-fluorohexyloxy)-phenyl-pyrimidine
No. 34. 2-(4'-Decylphenyl)-5-4'-(2"-fluorohexyloxy)-phenyl-pyrimidine
No. 35. 2-(4'-Undecylphenyl)-5-4'-(2"-fluorohexyloxy)-phenyl-pyrimidine
No. 36. 2-(4'-Dodecylphenyl)-5-4'-(2"-fluorohexyloxy)-phenyl-pyrimidine
No. 37. 2-(4'-Butylphenyl)-5-4'-(2"-fluoropropoxy)phenyl-pyrimidine
No. 38. 2-(4'-Pentylphenyl)-5-4'-(2"-fluoropropoxy)-phenyl-pyrimidine
No. 39. 2-(4'-Hexylphenyl)-5-4'-(2"-fluoropropoxy)phenyl-pyrimidine
No. 40. 2-(4'-Heptylphenyl)-5-4'-(2"-fluoropropoxy)-phenyl-pyrimidine
No. 41. 2-(4'-Octylphenyl)-5-4'-(2"-fluoropropoxy)phenyl-pyrimidine
No. 42. 2-(4'-Nonylphenyl)-5-4'-(2"-fluoropropoxy)-phenyl-pyrimidine
No. 43. 2-(4'-Decylphenyl)-5-4'-(2"-fluoropropoxy)phenyl-pyrimidine
No. 44. 2-(4'-Undecylphenyl)-5-4'-(2"-fluoropropoxy)-phenyl-pyrimidine
No. 45. 2-(4'-Dodecylphenyl)-5-4'-(2"-fluoropropoxy)-phenyl-pyrimidine
No. 46. 2-(4'-Butylphenyl)-5-4'-(2"-fluoroheptyloxy)-phenyl-pyrimidine
No. 47. 2-(4'-Pentylphenyl)-5-4'-(2"-fluoroheptyloxy)-phenyl-pyrimidine
No. 48. 2-(4'-Hexylphenyl)-5-4'-(2"-fluoroheptyloxy)-phenyl-pyrimidine
No. 49. 2-(4'-Heptylphenyl)-5-4'-(2"-fluoroheptyloxy)-phenyl-pyrimidine
No. 50. 2-(4'-Octylphenyl)-5-4'-(2"-fluoroheptyloxy)-phenyl-pyrimidine
No. 51. 2-(4'-Nonylphenyl)-5-4'-(2"-fluoroheptyloxy)-phenyl-pyrimidine
No. 52. 2-(4'-Decylphenyl)-5-4'-(2"-fluoroheptyloxy)-phenyl-pyrimidine
No. 53. 2-(4'-Undecylphenyl)-5-4'-(2"-fluoroheptyloxy)phenyl-pyrimidine
No. 54. 2-(4'-Dodecylphenyl)-5-4'-(2"-fluoroheptyloxy)phenyl-pyrimidine
No. 55. 2-(4'-Butylphenyl)-5-4'-(2"-fluorooctyloxy)phenyl-pyrimidine
No. 56. 2-(4'-Pentylphenyl)-5-4'-(2"-fluorooctyloxy)-phenyl-pyrimidine
No. 57. 2-(4'-Hexylphenyl)-5-4'-(2"-fluorooctyloxy)-phenyl-pyrimidine
No. 58. 2-(4'-Heptylphenyl)-5-4'-(2"-fluorooctyloxy)-phenyl-pyrimidine
No. 59. 2-(4'-Octylphenyl)-5-4'-(2"-fluorooctyloxy)phenyl-pyrimidine
No. 60. 2-(4'-Nonylphenyl)-5-4'-(2"-fluorooctyloxy)-phenyl-pyrimidine
No. 61. 2-(4'-Decylphenyl)-5-4'-(2"-fluorooctyloxy)-phenyl-pyrimidine
No. 62. 2-(4'-Undecylphenyl)-5-4'-(2"-fluorooctyloxy)-phenyl-pyrimidine
No. 63. 2-(4'-Dodecylphenyl)-5-4'-(2"-fluorooctyloxy)-phenyl-pyrimidine
No. 64. 2-(4'-Butylphenyl)-5-4'-(2"-fluorononyloxy)-phenyl-pyrimidine
No. 65. 2-(4'-Pentylphenyl)-5-4'-(2"-fluorononyloxy)-phenyl-pyrimidine
No. 66. 2-(4'-Hexylphenyl)-5-4'-(2"-fluorononyloxy)-phenyl-pyrimidine
No. 67. 2-(4'-Heptylphenyl)-5-4'-(2"-fluorononyloxy)-phenyl-pyrimidine
No. 68. 2-(4'-Octylphenyl)-5-4'-(2"-fluorononyloxy)-phenyl-pyrimidine
No. 69. 2-(4'-Nonylphenyl)-5-4'-(2"-fluorononyloxy)-phenyl-pyrimidine
No. 70. 2-(4'-Decylphenyl)-5-4'-(2"-fluorononyloxy)-phenyl-pyrimidine
No. 71. 2-(4'-Undecylphenyl)-5-4'-(2"-fluorononyloxy)-phenyl-pyrimidine
No. 72. 2-(4'-Dodecylphenyl)-5-4'-(2"-fluorononyloxy)-phenyl-pyrimidine
No. 73. 2-(4'-Butylphenyl)-5-4'-(2"-fluorodecyloxy)-phenyl-pyrimidine
No. 74. 2-(4'-Pentylphenyl)-5-4'-(2"-fluorodecyloxy)-phenyl-pyrimidine
No. 75. 2-(4'-Hexylphenyl)-5-4'-(2"-fluorodecyloxy)-phenyl-pyrimidine
No. 76. 2-(4'-Heptylphenyl)-5-4'-(2"-fluorodecyloxy)-phenyl-pyrimidine
No. 77. 2-(4'-Octylphenyl)-5-4'-(2"-fluorodecyloxy)-phenyl-pyrimidine
No. 78. 2-(4'-Nonylphenyl)-5-4'-(2"-fluorodecyloxy)-phenyl-pyrimidine
No. 79. 2-(4'-Decylphenyl)-5-4'-(2"-fluorodecyloxy)-phenyl-pyrimidine
No. 80. 2-(4'-Undecylphenyl)-5-4'-(2"-fluorodecyloxy)-phenyl-pyrimidine
No. 81. 2-(4'-Dodecylphenyl)-5-4'-(2"-fluorodecyloxy)-phenyl-pyrimidine
No. 82. 2-(4'-Butylphenyl)-5-4'-(2"-fluoroundecyloxy)-phenyl-pyrimidine
No. 83. 2-(4'-Pentylphenyl)-5-4'-(2"-fluoroundecyloxy)-phenyl-pyrimidine
No. 84. 2-(4'-Hexylphenyl)-5-4'-(2"-fluoroundecyloxy)-phenyl-pyrimidine No. 85. 2-(4'-Heptylphenyl)-5-4'-(2''-fluoroundecyloxy)phenyl-pyrimidine
No. 86. 2-(4'-Octylphenyl)-5-4'-(2''-fluoroundecyloxy)phenyl-pyrimidine
No. 87. 2-(4'-Nonylphenyl)-5-4'-(2''-fluoroundecyloxy)phenyl-pyrimidine
No. 88. 2-(4'-Decylphenyl)-5-4'-(2''-fluoroundecyloxy)phenyl-pyrimidine
No. 89. 2-(4'-Undecylphenyl)-5-4'-(2''-fluoroundecyloxy)phenyl-pyrimidine
No. 90. 2-(4'-Dodecylphenyl)-5-4'-(2''-fluoroundecyloxy)phenyl-pyrimidine
No. 91. 2-(4'-Butylphenyl)-5-4'-(2''-fluorododecyloxy)phenyl-pyrimidine
No. 92. 2-(4'-Pentylphenyl)-5-4'-(2''-fluorododecyloxy)phenyl-pyrimidine
No. 93. 2-(4'-Hexylphenyl)-5-4'-(2''-fluorododecyloxy)phenyl-pyrimidine
No. 94. 2-(4'-Heptylphenyl)-5-4'-(2''-fluorododecyloxy)phenyl-pyrimidine
No. 95. 2-(4'-Octylphenyl)-5-4'-(2''-fluorododecyloxy)phenyl-pyrimidine
No. 96. 2-(4'-Nonylphenyl)-5-4'-(2''-fluorododecyloxy)phenyl-pyrimidine
No. 97. 2-(4'-Decylphenyl)-5-4'-(2''-fluorododecyloxy)phenyl-pyrimidine
No. 98. 2-(4'-Undecylphenyl)-5-4'-(2''-fluorododecyloxy)phenyl-pyrimidine
No. 99. 2-(4'-Dodecylphenyl)-5-4'-(2''-fluorododecyloxy)phenyl-pyrimidine
No. 100. 2-(4'-Butylphenyl)-5-4'-(2''-fluoro-3''-methylbutoxy)phenyl-pyrimidine
No. 101. 2-(4'-Pentylphenyl)-5-4'-(2''-fluoro-3''-methylbutoxy)phenyl-pyrimidine
No. 102. 2-(4'-Hexylphenyl)-5-4'-(2''-fluoro-3''-methylbutoxy)phenyl-pyrimidine
No. 103. 2-(4'-Heptylphenyl)-5-4'-(2''-fluoro-3''-methylbutoxy)phenyl-pyrimidine
No. 104. 2-(4'-Octylphenyl)-5-4'-(2''-fluoro-3''-methylbutoxy)phenyl-pyrimidine
No. 105. 2-(4'-Nonylphenyl)-5-4'-(2''-fluoro-3''-methylbutoxy)phenyl-pyrimidine
No. 106. 2-(4'-Decylphenyl)-5-4'-(2''-fluoro-3''-methylbutoxy)phenyl-pyrimidine
No. 107. 2-(4'-Undecylphenyl)-5-4'-(2''-fluoro-3''-methylbutoxy)phenyl-pyrimidine
No. 108. 2-(4'-Dodecylphenyl)-5-4'-(2''-fluoro-3''-methylbutoxy)phenyl-pyrimidine
No. 109. 2-(4'-Butylphenyl)-5-4'-(2''-fluoro-3''-methylpentoxy)phenyl-pyrimidine
No. 110. 2-(4'-Pentylphenyl)-5-4'-(2''-fluoro-3''-methylpentoxy)phenyl-pyrimidine
No. 111. 2-(4'-Hexylphenyl)-5-4'-(2''-fluoro-3''-methylpentoxy)phenyl-pyrimidine
No. 112. 2-(4'-Heptylphenyl)-5-4'-(2''-fluoro-3''-methylpentoxy)phenyl-pyrimidine
No. 113. 2-(4'-Octylphenyl)-5-4'-(2''-fluoro-3''-methylpentoxy)phenyl-pyrimidine
No. 114. 2-(4'-Nonylphenyl)-5-4'-(2''-fluoro-3''-methylpentoxy)phenyl-pyrimidine
No. 115. 2-(4'-Decylphenyl)-5-4'-(2''-fluoro-3''-methylpentoxy)phenyly-pyrimidine
No. 116. 2-(4'-Undecylphenyl)-5-4'-(2''-fluoro-3''-methylpentoxy)phenyl-pyrimidine
No. 117. 2-(4'-Dodecylphenyl)-5-4'-(2''-fluoro-3''-methylpentoxy)phenyl-pyrimidine
No. 118. 2-(4'-Butylphenyl)-5-4'-(2''-fluoro-4''-methylpentoxy)phenyl-pyrimidine
No. 119. 2-(4'-Pentylphenyl)-5-4'-(2''-fluoro-4''-methylpentoxy)phenyl-pyrimidine
No. 120. 2-(4'-Hexylphenyl)-5-4'-(2''-fluoro-4''-methylpentoxy)phenyl-pyrimidine
No. 121. 2-(4'-Heptylphenyl)-5-4'-(2''-fluoro-4''-methylpentoxy)phenyl-pyrimidine
No. 122. 2-(4'-Octylphenyl)-5-4'-(2''-fluoro-4''-methylpentoxy)phenyl-pyrimidine
No. 123. 2-(4'-Nonylphenyl)-5-4'-(2''-fluoro-4''-methylpentoxy)phenyl-pyrimidine
No. 124. 2-(4'-Decylphenyl)-5-4'-(2''-fluoro-4''-methylpentoxy)phenyly-pyrimidine
No. 125. 2-(4'-Undecylphenyl)-5-4'-(2''-fluoro-4''-methylpentoxy)phenyl-pyrimidine
No. 126. 2-(4'-Dodecylphenyl)-5-4'-(2''-fluoro-4''-methylpentoxy)phenyl-pyrimidine
No. 127. 2-(4'-Butoxyphenyl)-5-4'-(2''-fluoropropoxy)phenyl-pyrimidinene
No. 128. 2-(4'-Pentoxyphenyl)-5-4'-(2''-fluoropropoxy)phenyl-pyrimidinene
No. 129. 2-(4'-Hexyloxyphenyl)-5-4'-(2''-fluoropropoxy)phenyl-pyrimidine
No. 130. 2-(4'-Heptyloxyphenyl)-5-4'-(2''-fluoropropoxy)phenyl-pyrimidine
No. 131. 2-(4'-Octyloxyphenyl)-5-4'-(2''-fluoropropoxy)phenyl-pyrimidine
No. 132. 2-(4'-Nonyloxyphenyl)-5-4'-(2''-fluoropropoxy)phenyl-pyrimidine
No. 133. 2-(4'-Decyloxyphenyl)-5-4'-(2''-fluoropropoxy)phenyl-pyrimidine
No. 134. 2-(4'-Undecyloxyphenyl)-5-4'-(2''-fluoropropoxy)phenyl-pyrimidine
No. 135. 2-(4'-Dodecyloxyphenyl)-5-4'-(2''-fluoropropoxy)phenyl-pyrimidine
No. 136. 2-(4'-Butoxyphenyl)-5-4'-(2''-fluorobutoxy)phenyl-pyrimidinene
No. 137. 2-(4'-Pentoxyphenyl)-5-4'-(2''-fluorobutoxy)phenyl-pyrimidinene
No. 138. 2-(4'-Hexyloxyphenyl)-5-4'-(2''-fluorobutoxy)phenyl-pyrimidine
No. 139. 2-(4'-Heptyloxyphenyl)-5-4'-(2''-fluorobutoxy)phenyl-pyrimidine
No. 140. 2-(4'-Octyloxyphenyl)-5-4'-(2''-fluorobutoxy)phenyl-pyrimidine
No. 141. 2-(4'-Nonyloxyphenyl)-5-4'-(2''-fluorobutoxy)phenyl-pyrimidine
No. 142. 2-(4'-Decyloxyphenyl)-5-4'-(2''-fluorobutoxy)phenyl-pyrimidine
No. 143. 2-(4'-Undecyloxyphenyl)-5-4'-(2''-fluorobutoxy)phenyl-pyrimidine
No. 144. 2-(4'-Dodecyloxyphenyl)-5-4'-(2''-fluorobutoxy)phenyl-pyrimidine
No. 145. 2-(4'-Butoxyphenyl)-5-4'-(2''-fluoropentoxy)phenyl-pyrimidinene
No. 146. 2-(4'-Pentoxyphenyl)-5-4'-(2''-fluoropentoxy)phenyl-pyrimidinene
No. 147. 2-(4'-Hexyloxyphenyl)-5-4'-(2''-fluoropentoxy)phenyl-pyrimidine
No. 148. 2-(4'-Heptyloxyphenyl)-5-4'-(2''-fluoropentoxy)phenyl-pyrimidine
No. 149. 2-(4'-Octyloxyphenyl)-5-4'-(2''-fluoropentoxy)phenyl-pyrimidine
No. 150. 2-(4'-Nonyloxyphenyl)-5-4'-(2''-fluoropentoxy)phenyl-pyrimidine
No. 151. 2-(4'-Decyloxyphenyl)-5-4'-(2''-fluoropentoxy)phenyl-pyrimidine
No. 152. 2-(4'-Undecyloxyphenyl)-5-4'-(2''-fluoropentoxy)phenyl-pyrimidine No. 153. 2-(4'-Dodecyloxyphenyl)-5-4'-(2"-fluoropentoxy)phenyl-pyrimidine
No. 154. 2-(4'-Butoxyphenyl)-5-4'-(2"-fluorohexyloxy)phenyl-pyrimidinene
No. 155. 2-(4'-Pentoxyphenyl)-5-4'-(2"-fluorohexyloxy)phenyl-pyrimidinene
No. 156. 2-(4'-Hexyloxyphenyl)-5-4'-(2"-fluorohexyloxy)phenyl-pyrimidine
No. 157. 2-(4'-Heptyloxyphenyl)-5-4'-(2"-fluorohexyloxy)phenyl-pyrimidine
No. 158. 2-(4'-Octyloxyphenyl)-5-4'-(2"-fluorohexyloxy)phenyl-pyrimidine
No. 159. 2-(4'-Nonyloxyphenyl)-5-4'-(2"-fluorohexyloxy)phenyl-pyrimidine
No. 160. 2-(4'-Decyloxyphenyl)-5-4'-(2"-fluorohexyloxy)phenyl-pyrimidine
No. 161. 2-(4'-Undecyloxyphenyl)-5-4'-(2"-fluorohexyloxy)phenyl-pyrimidine
No. 162. 2-(4'-Dodecyloxyphenyl)-5-4'-(2"-fluorohexyloxy)phenyl-pyrimidine
No. 163. 2-(4'-Butoxyphenyl)-5-4'-(2"-fluoroheptyloxy)phenyl-pyrimidinene
No. 164. 2-(4'-Pentoxyphenyl)-5-4'-(2"-fluoroheptyloxy)phenyl-pyrimidinene
No. 165. 2-(4'-Hexyloxyphenyl)-5-4'-(2"-fluoroheptyloxy)phenyl-pyrimidine
No. 166. 2-(4'-Heptyloxyphenyl)-5-4'-(2"-fluoroheptyloxy)phenyl-pyrimidine
No. 167. 2-(4'-Octyloxyphenyl)-5-4'-(2"-fluoroheptyloxy)phenyl-pyrimidine
No. 168. 2-(4'-Nonyloxyphenyl)-5-4'-(2"-fluoroheptyloxy)phenyl-pyrimidine
No. 169. 2-(4'-Decyloxyphenyl)-5-4'-(2"-fluoroheptyloxy)phenyl-pyrimidine
No. 170. 2-(4'-Undecyloxyphenyl)-5-4'-(2"-fluoroheptyloxy)phenyl-pyrimidine
No. 171. 2-(4'-Dodecyloxyphenyl)-5-4'-(2"-fluoroheptyloxy)phenyl-pyrimidine
No. 172. 2-(4'-Butoxyphenyl)-5-4'-(2"-fluorooctyloxy)phenyl-pyrimidine
No. 173. 2-(4'-Pentoxyphenyl)-5-4'-(2"-fluorooctyloxy)phenyl-pyrimidine
No. 174. 2-(4'-Hexyloxyphenyl)-5-4'-(2"-fluorooctyloxy)phenyl-pyrimidine
No. 175. 2-(4'-Heptyloxyphenyl)-5-4'-(2"-fluorooctyloxy)phenyl-pyrimidine
No. 176. 2-(4'-Octyloxyphenyl)-5-4'-(2"-fluorooctyloxy)phenyl-pyrimidine
No. 177. 2-(4'-Nonyloxyphenyl)-5-4'-(2"-fluorooctyloxy)phenyl-pyrimidine
No. 178. 2-(4'-Decyloxyphenyl)-5-4'-(2"-fluorooctyloxy)phenyl-pyrimidine
No. 179. 2-(4'-Undecyloxyphenyl)-5-4'-(2"-fluorooctyloxy)phenyl-pyrimidine
No. 180. 2-(4'-Dodecyloxyphenyl)-5-4'-(2"-fluorooctyloxy)phenyl-pyrimidine
No. 181. 2-(4'-Butoxyphenyl)-5-4'-(2"-fluorononyloxy)phenyl-pyrimidine
No. 182. 2-(4'-Pentoxyphenyl)-5-4'-(2"-fluorononyloxy)phenyl-pyrimidine
No. 183. 2-(4'-Hexyloxyphenyl)-5-4'-(2"-fluorononyloxy)phenyl-pyrimidine
No. 184. 2-(4'-Heptyloxyphenyl)-5-4'-(2"-fluorononyloxy)phenyl-pyrimidine
No. 185. 2-(4'-Octyloxyphenyl)-5-4'-(2"-fluorononyloxy)phenyl-pyrimidine
No. 186. 2-(4'-Nonyloxyphenyl)-5-4'-(2"-fluorononyloxy)phenyl-pyrimidine
No. 187. 2-(4'-Decyloxyphenyl)-5-4'-(2"-fluorononyloxy)phenyl-pyrimidine
No. 188. 2-(4'-Undecyloxyphenyl)-5-4'-(2"-fluorononyloxy)phenyl-pyrimidine
No. 189. 2-(4'-Dodecyloxyphenyl)-5-4'-(2"-fluorononyloxy)phenyl-pyrimidine
No. 190. 2-(4'-Butoxyphenyl)-5-4'-(2"-fluorodecyloxy)phenyl-pyrimidinene
No. 191. 2-(4'-Pentoxyphenyl)-5-4'-(2"-fluorodecyloxy)phenyl-pyrimidinene
No. 192. 2-(4'-Hexyloxyphenyl)-5-4'-(2"-fluorodecyloxy)phenyl-pyrimidine
No. 193. 2-(4'-Heptyloxyphenyl)-5-4'-(2"-fluorodecyloxy)phenyl-pyrimidine
No. 194. 2-(4'-Octyloxyphenyl)-5-4'-(2"-fluorodecyloxy)phenyl-pyrimidine
No. 195. 2-(4'-Nonyloxyphenyl)-5-4'-(2"-fluorodecyloxy)phenyl-pyrimidine
No. 196. 2-(4'-Decyloxyphenyl)-5-4'-(2"-fluorodecyloxy)phenyl-pyrimidine
No. 197. 2-(4'-Undecyloxyphenyl)-5-4'-(2"-fluorodecyloxy)phenyl-pyrimidine
No. 198. 2-(4'-Dodecyloxyphenyl)-5-4'-(2"-fluorodecyloxy)phenyl-pyrimidine
No. 199. 2-(4'-Butoxyphenyl)-5-4'-(2"-fluoroundecyloxy)phenyl-pyrimidinene
No. 200. 2-(4'-Pentoxyphenyl)-5-4'-(2"-fluoroundecyloxy)phenyl-pyrimidinene
No. 201. 2-(4'-Hexyloxyphenyl)-5-4'-(2"-fluoroundecyloxy)phenyl-pyrimidine
No. 202. 2-(4'-Heptyloxyphenyl)-5-4'-(2"-fluoroundecyloxy)phenyl-pyrimidine
No. 203. 2-(4'-Octyloxyphenyl)-5-4'-(2"-fluoroundecyloxy)phenyl-pyrimidine
No. 204. 2-(4'-Nonyloxyphenyl)-5-4'-(2"-fluoroundecyloxy)phenyl-pyrimidine
No. 205. 2-(4'-Decyloxyphenyl)-5-4'-(2"-fluoroundecyloxy)phenyl-pyrimidine
No. 206. 2-(4'-Undecyloxyphenyl)-5-4'-(2"-fluoroundecyloxy)phenyl-pyrimidine
No. 207. 2-(4'-Dodecyloxyphenyl)-5-4'-(2"-fluoroundecyloxy)phenyl-pyrimidine
No. 208. 2-(4'-Butoxyphenyl)-5-4'-(2"-fluorododecyloxy)phenyl-pyrimidinene
No. 209. 2-(4'-Pentoxyphenyl)-5-4'-(2"-fluorododecyloxy)phenyl-pyrimidinene
No. 210. 2-(4'-Hexyloxyphenyl)-5-4'-(2"-fluorododecyloxy)phenyl-pyrimidine
No. 211. 2-(4'-Heptyloxyphenyl)-5-4'-(2"-fluorododecyloxy)phenyl-pyrimidine
No. 212. 2-(4'-Octyloxyphenyl)-5-4'-(2"-fluorododecyloxy)phenyl-pyrimidine
No. 213. 2-(4'-Nonyloxyphenyl)-5-4'-(2"-fluorododecyloxy)phenyl-pyrimidine
No. 214. 2-(4'-Decyloxyphenyl)-5-4'-(2"-fluorododecyloxy)phenyl-pyrimidine
No. 215. 2-(4'-Undecyloxyphenyl)-5-4'-(2"-fluorododecyloxy)phenyl-pyrimidine
No. 216. 2-(4'-Dodecyloxyphenyl)-5-4'-(2"-fluorododecyloxy)phenyl-pyrimidine
No. 217. 2-(4'-Butoxyphenyl)-5-4'-(2"-fluoro-3"-methylbutoxy)phenyl-pyrimidine
No. 218. 2-(4'-Pentoxyphenyl)-5-4'-(2"-fluoro-3"-methylbutoxy)phenyl-pyrimidine
No. 219. 2-(4'-Hexyloxyphenyl)-5-4'-(2"-fluoro-3"-methylbutoxy)phenyl-pyrimidine
No. 220. 2-(4'-Heptyloxyphenyl)-5-4'-(2"-fluoro-3"-methylbutoxy)phenyl-pyrimidine No. 221. 2-(4'-Octyloxyphenyl)-5-4'-(2''-fluoro-3''-methylbutoxy)phenyl-pyrimidine
No. 222. 2-(4'-Nonyloxyphenyl)-5-4'-(2''-fluoro-3''-methylbutoxy)phenyl-pyrimidine
No. 223. 2-(4'-Decyloxyphenyl)-5-4'-(2''-fluoro-3''-methylbutoxy)phenyl-pyrimidine
No. 224. 2-(4'-Undecyloxyphenyl)-5-4'-(2''-fluoro-3''-methylbutoxy)phenyl-pyrimidine
No. 225. 2-(4'-Dodecyloxyphenyl)-5-4'-(2''-fluoro-3''-methylbutoxy)phenyl-pyrimidine
No. 226. 2-(4'-Butoxyphenyl)-5-4'-(2''-fluoro-3''-methylpentoxy)phenyl-pyrimidine
No. 227. 2-(4'-Pentoxyphenyl)-5-4'-(2''-fluoro-3''-methylpentoxy)phenyl-pyrimidine
No. 228. 2-(4'-Hexyloxyphenyl)-5-4'-(2''-fluoro-3''-methylpentoxy)phenyl-pyrimidine
No. 229. 2-(4'-Heptyloxyphenyl)-5-4'-(2''-fluoro-3''-methylpentoxy)phenyl-pyrimidine
No. 230. 2-(4'-Octyloxyphenyl)-5-4'-(2''-fluoro-3''-methylpentoxy)phenyl-pyrimidine
No. 231. 2-(4'-Nonyloxyphenyl)-5-4'-(2''-fluoro-3''-methylpentoxy)phenyl-pyrimidine
No. 232. 2-(4'-Decyloxyphenyl)-5-4'-(2''-fluoro-3''-methylpentoxy)phenyl-pyrimidine
No. 233. 2-(4'-Undecyloxyphenyl)-5-4'-(2''-fluoro-3''-methylpentoxy)phenyl-pyrimidine
No. 234. 2-(4'-Dodecyloxyphenyl)-5-4'-(2''-fluoro-3''-methylpentoxy)phenyl-pyrimidine
No. 235. 2-(4'-Butoxyphenyl)-5-4'-(2''-fluoro-4''-methylpentoxy)phenyl-pyrimidine
No. 236. 2-(4'-Pentoxyphenyl)-5-4'-(2''-fluoro-4''-methylpentoxy)phenyl-pyrimidine
No. 237. 2-(4'-Hexyloxyphenyl)-5-4'-(2''-fluoro-4''-methylpentoxy)phenyl-pyrimidine
No. 238. 2-(4'-Heptyloxyphenyl)-5-4'-(2''-fluoro-4''-methylpentoxy)phenyl-pyrimidine
No. 239. 2-(4'-Octyloxyphenyl)-5-4'-(2''-fluoro-4''-methylpentoxy)phenyl-pyrimidine
No. 240. 2-(4'-Nonyloxyphenyl)-5-4'-(2''-fluoro-4''-methylpentoxy)phenyl-pyrimidine
No. 241. 2-(4'-Decyloxyphenyl)-5-4'-(2''-fluoro-4''-methylpentoxy)phenyl-pyrimidine
No. 242. 2-(4'-Undecyloxyphenyl)-5-4'-(2''-fluoro-4''-methylpentoxy)phenyl-pyrimidine
No. 243. 2-(4'-Dodecyloxyphenyl)-5-4'-(2''-fluoro-4''-methylpentoxy)phenyl-pyrimidine
No. 244. 2-4'-(2''-Fluoropropoxy)phenyl-5-(4'-butylphenyl)-pyrimidine
No. 245. 2-4'-(2''-Fluoropropoxy)phenyl-5-(4'-pentylphenyl)-pyrimidine
No. 246. 2-4'-(2''-Fluoropropoxy)phenyl-5-(4'-hexylphenyl)-pyrimidine
No. 247. 2-4'-(2''-Fluoropropoxy)phenyl-5-(4'-heptylphenyl)-pyrimidine
No. 248. 2-4'-(2''-Fluoropropoxy)phenyl-5-(4'-octylphenyl)-pyrimidine
No. 249. 2-4'-(2''-Fluoropropoxy)phenyl-5-(4'-nonylphenyl)-pyrimidine
No. 250. 2-4'-(2''-Fluoropropoxy)phenyl-5-(4'-decylphenyl)-pyrimidine
No. 251. 2-4'-(2''-Fluoropropoxy)phenyl-5-(4'-undecylphenyl)-pyrimidine
No. 252. 2-4'-(2''-Fluoropropoxy)phenyl-5-(4'-dodecylphenyl)-pyrimidine
No. 253. 2-4'-(2''-Fluorobutoxy)phenyl-5-(4'-butylphenyl)-pyrimidine
No. 254. 2-4'-(2''-Fluorobutoxy)phenyl-5-(4'-pentylphenyl)-pyrimidine
No. 255. 2-4'-(2''-Fluorobutoxy)phenyl-5-(4'-hexylphenyl)-pyrimidine
No. 256. 2-4'-(2''-Fluorobutoxy)phenyl-5-(4'-heptylphenyl)-pyrimidine
No. 275. 2-4'-(2''-Fluorobutoxy)phenyl-5-(4'-octylphenyl)-pyrimidine
No. 258. 2-4'-(2''-Fluorobutoxy)phenyl-5-(4'-nonylphenyl)-pyrimidine
No. 259. 2-4'-(2''-Fluorobutoxy)phenyl-5-(4'-decylphenyl)-pyrimidine
No. 260. 2-4'-(2''-Fluorobutoxy)phenyl-5-(4'-undecylphenyl)-pyrimidine
No. 261. 2-4'-(2''-Fluorobutoxy)phenyl-5-(4'-dodecylphenyl)-pyrimidine
No. 262. 2-4'-(2''-Fluoropentoxy)phenyl-5-(4'-butylphenyl)-pyrimidine
No. 263. 2-4'-(2''-Fluoropentoxy)phenyl-5-(4'-pentylphenyl)-pyrimidine
No. 264. 2-4'-(2''-Fluoropentoxy)phenyl-5-(4'-hexylphenyl)-pyrimidine
No. 265. 2-4'-(2''-Fluoropentoxy)phenyl-5-(4'-heptylphenyl)-pyrimidine
No. 266. 2-4'-(2''-Fluoropentoxy)phenyl-5-(4'-octylphenyl)-pyrimidine
No. 267. 2-4'-(2''-Fluoropentoxy)phenyl-5-(4'-nonylphenyl)-pyrimidine
No. 268. 2-4'-(2''-Fluoropentoxy)phenyl-5-(4'-decylphenyl)-pyrimidine
No. 269. 2-4'-(2''-Fluoropentoxy)phenyl-5-(4'-undecylphenyl)-pyrimidine
No. 270. 2-4'-(2''-Fluoropentoxy)phenyl-5-(4'-dodecylphenyl)-pyrimidine
No. 271. 2-4'-(2''-Fluorohexyloxy)phenyl-5-(4'-butylphenyl)-pyrimidine
No. 272. 2-4'-(2''-Fluorohexyloxy)phenyl-5-(4'-pentylphenyl)-pyrimidine
No. 273. 2-4'-(2''-Fluorohexyloxy)phenyl-5-(4'-hexylphenyl)-pyrimidine
No. 274. 2-4'-(2''-Fluorohexyloxy)phenyl-5-(4'-heptylphenyl)-pyrimidine
No. 275. 2-4'-(2''-Fluorohexyloxy)phenyl-5-(4'-octylphenyl)-pyrimidine
No. 276. 2-4'-(2''-Fluorohexyloxy)phenyl-5-(4'-nonylphenyl)-pyrimidine
No. 277. 2-4'-(2''-Fluorohexyloxy)phenyl-5-(4'-decylphenyl)-pyrimidine
No. 278. 2-4'-(2''-Fluorohexyloxy)phenyl-5-(4'-undecylphenyl)-pyrimidine
No. 279. 2-4'-(2''-Fluorohexyloxy)phenyl-5-(4'-dodecylphenyl)-pyrimidine
No. 280. 2-4'-(2''-Fluoroheptyloxy)phenyl-5-(4'-butylphenyl)-pyrimidine
No. 281. 2-4'-(2''-Fluoroheptyloxy)phenyl-5-(4'-pentylphenyl)-pyrimidine
No. 282. 2-4'-(2''-Fluoroheptyloxy)phenyl-5-(4'-hexylphenyl)-pyrimidine
No. 283. 2-4'-(2''-Fluoroheptyloxy)phenyl-5-(4'-heptylphenyl)-pyrimidine
No. 284. 2-4'-(2''-Fluoroheptyloxy)phenyl-5-(4'-octylphenyl)-pyrimidine
No. 285. 2-4'-(2''-Fluoroheptyloxy)phenyl-5-(4'-nonylphenyl)-pyrimidine
No. 286. 2-4'-(2''-Fluoroheptyloxy)phenyl-5-(4'-decylphenyl)-pyrimidine
No. 287. 2-4'-(2''-Fluoroheptyloxy)phenyl-5-(4'-undecylphenyl)-pyrimidine
No. 288. 2-4'-(2''-Fluoroheptyloxy)phenyl-5-(4'-dodecylphenyl)-pyrimidine No. 289. 2-4'-(2''-Fluorooctyloxy)phenyl-5-(4'-butylphenyl)-pyrimidine
No. 290. 2-4'-(2''-Fluorooctyloxy)phenyl-5-(4'-pentylphenyl)-pyrimidine
No. 291. 2-4'-(2''-Fluorooctyloxy)phenyl-5-(4'-hexylphenyl)-pyrimidine
No. 292. 2-4'-(2''-Fluorooctyloxy)phenyl-5-(4'-heptylphenyl)-pyrimidine
No. 293. 2-4'-(2''-Fluorooctyloxy)phenyl-5-(4'-octylphenyl)-pyrimidine
No. 294. 2-4'-(2''-Fluorooctyloxy)phenyl-5-(4'-nonylphenyl)-pyrimidine
No. 295. 2-4'-(2''-Fluorooctyloxy)phenyl-5-(4'-decylphenyl)-pyrimidine
No. 296. 2-4'-(2''-Fluorooctyloxy)phenyl-5-(4'-undecylphenyl)-pyrimidine
No. 297. 2-4'-(2''-Fluorooctyloxy)phenyl-5-(4'-dodecylphenyl)-pyrimidine
No. 298. 2-4'-(2''-Fluorononyloxy)phenyl-5-(4'-butylphenyl)-pyrimidine
No. 299. 2-4'-(2''-Fluorononyloxy)phenyl-5-(4'-pentylphenyl)-pyrimidine
No. 300. 2-4'-(2''-Fluorononyloxy)phenyl-5-(4'-hexylphenyl)-pyrimidine
No. 301. 2-4'-(2''-Fluorononyloxy)phenyl-5-(4'-heptylphenyl)-pyrimidine
No. 302. 2-4'-(2''-Fluorononyloxy)phenyl-5-(4'-octylphenyl)-pyrimidine
No. 303. 2-4'-(2''-Fluorononyloxy)phenyl-5-(4'-nonylphenyl)-pyrimidine
No. 304. 2-4'-(2''-Fluorononyloxy)phenyl-5-(4'-decylphenyl)-pyrimidine
No. 305. 2-4'-(2''-Fluorononyloxy)phenyl-5-(4'-undecylphenyl)-pyrimidine
No. 306. 2-4'-(2''-Fluorononyloxy)phenyl-5-(4'-dodecylphenyl)-pyrimidine
No. 307. 2-4'-(2''-Fluorodecyloxy)phenyl-5-(4'-butylphenyl)-pyrimidine
No. 308. 2-4'-(2''-Fluorodecyloxy)phenyl-5-(4'-pentylphenyl)-pyrimidine
No. 309. 2-4'-(2''-Fluorodecyloxy)phenyl-5-(4'-hexylphenyl)-pyrimidine
No. 310. 2-4'-(2''-Fluorodecyloxy)phenyl-5-(4'-heptylphenyl)-pyrimidine
No. 311. 2-4'-(2''-Fluorodecyloxy)phenyl-5-(4'-octylphenyl)-pyrimidine
No. 312. 2-4'-(2''-Fluorodecyloxy)phenyl-5-(4'-nonylphenyl)-pyrimdine
No. 313. 2-4'-(2''-Fluorodecyloxy)phenyl-5-(4'-decylphenyl)-pyrimidine
No. 314. 2-4'-(2''-Fluorodecyloxy)phenyl-5-(4'-undecylphenyl)-pyrimidine
No. 315. 2-4'-(2''-Fluorodecyloxy)phenyl-5-(4'-dodecylphenyl)-pyrimidine
No. 316. 2-4'-(2''-Fluoroundecyloxy)phenyl-5-(4'-butylphenyl)-pyrimidine
No. 317. 2-4'-(2''-Fluoroundecyloxy)phenyl-5-(4'-pentylphenyl)-pyrimidine
No. 318. 2-4'-(2''-Fluoroundecyloxy)phenyl-5-(4'-hexylphenyl)-pyrimidine
No. 319. 2-4'-(2''-Fluoroundecyloxy)phenyl-5-(4'-heptylphenyl)-pyrimidine
No. 320. 2-4'-(2''-Fluoroundecyloxy)phenyl-5-(4'-octylphenyl)-pyrimidine
No. 321. 2-4'-(2''-Fluoroundecyloxy)phenyl-5-(4'-nonylphenyl)-pyrimidine
No. 322. 2-4'-(2''-Fluoroundecyloxy)phenyl-5-(4'-decylphenyl)-pyrimidine
No. 323. 2-4'-(2''-Fluoroundecyloxy)phenyl-5-(4'-undecylphenyl)-pyrimidine
No. 324. 2-4'-(2''-Fluoroundecyloxy)phenyl-5-(4'-dodecylphenyl)-pyrimidine
No. 325. 2-4'-(2''-Fluorododecyloxy)phenyl-5-(4'-butylphenyl)-pyrimidine
No. 326. 2-4'-(2''-Fluorododecyloxy)phenyl-5-(4'-pentylphenyl)-pyrimidine
No. 327. 2-4'-(2''-Fluorododecyloxy)phenyl-5-(4'-hexylphenyl)-pyrimidine
No. 328. 2-4'-(2''-Fluorododecyloxy)phenyl-5-(4'-heptylphenyl)-pyrimidine
No. 329. 2-4'-(2''-Fluorododecyloxy)phenyl-5-(4'-octylphenyl)-pyrimidine
No. 330. 2-4'-(2''-Fluorododecyloxy)phenyl-5-(4'-nonylphenyl)-pyrimidine
No. 331. 2-4'-(2''-Fluorododecyloxy)phenyl-5-(4'-decylphenyl)-pyrimidine
No. 332. 2-4'-(2''-Fluorododecyloxy)phenyl-5-(4'-undecylphenyl)-pyrimidine
No. 333. 2-4'-(2''-Fluorododecyloxy)phenyl-5-(4'-dodecylphenyl)-pyrimidine
No. 334. 2-4'-(2''-Fluoro-3''methylbutoxy)phenyl-5-(4'-butylphenyl)-pyrimidine
No. 335. 2-4'-(2''-Fluoro-3''methylbutoxy)phenyl-5-(4'-pentylphenyl)-pyrimidine
No. 336. 2-4'-(2''-Fluoro-3''methylbutoxy)phenyl-5-(4'-hexylphenyl)-pyrimidine
No. 337. 2-4'-(2''-Fluoro-3''methylbutoxy)phenyl-5-(4'-heptylphenyl)-pyrimidine
No. 338. 2-4'-(2''-Fluoro-3''methylbutoxy)phenyl-5-(4'-octylphenyl)-pyrimidine
No. 339. 2-4'-(2''-Fluoro-3''methylbutoxy)phenyl-5-(4'-nonylphenyl)-pyrimidine
No. 340. 2-4'-(2''-Fluoro-3''methylbutoxy)phenyl-5-(4'-decylphenyl)-pyrimidine
No. 341. 2-4'-(2''-Fluoro-3''methylbutoxy)phenyl-5-(4'-undecylphenyl)-pyrimidine
No. 342. 2-4'-(2''-Fluoro-3''methylbutoxy)phenyl-5-(4'-dodecylphenyl)-pyrimidine
No. 343. 2-4'-(2''-Fluoro-3''methylpentoxy)phenyl-5-(4'-butylphenyl)-pyrimidine
No. 344. 2-4'-(2''-Fluoro-3''methylpentoxy)phenyl-5-(4'-pentylphenyl)-pyrimidine
No. 345. 2-4'-(2''methylpentoxy)phenyl-5-(4'-hexylphenyl)-pyrimidine
No. 346. 2-4'-(2''-Fluoro-3''methylpentoxy)phenyl-5-(4'-heptylphenyl)-pyrimidine
No. 347. 2-4'-(2''-Fluoro-3''methylpentoxy)phenyl-5-(4'-octylphenyl)-pyrimidine
No. 348. 2-4'-(2''-Fluoro-3''methylpentoxy)phenyl-5-(4'-nonylphenyl)-pyrimidine
No. 349. 2-4'-(2''-Fluoro-3''methylpentoxy)phenyl-5-(4'-decylphenyl)-pyrimidine
No. 350. 2-4'-(2''-Fluoro-3''methylpentoxy)phenyl-5-(4'-undecylphenyl)-pyrimidine
No. 351. 2-4'-(2''-Fluoro-3''methylpentoxy)phenyl-5-(4'-dodecylphenyl)-pyrimidine
No. 352. 2-4'-(2''-Fluoro-4''methylpentoxy)phenyl-5-(4'-butylphenyl)-pyrimidine
No. 353. 2-4'-(2''-Fluoro-4''methylpentoxy)phenyl-5-(4'-pentylphenyl)-pyrimidine
No. 354. 2-4'-(2''-Fluoro-4''methylpentoxy)phenyl-5-(4'-hexylphenyl)-pyrimidine
No. 355. 2-4'-(2''-Fluoro-4''methylpentoxy)phenyl-5-(4'-heptylphenyl)-pyrimidine
No. 356. 2-4'-(2''-Fluoro-4''methylpentoxy)phenyl-5-(4'-octylphenyl)-pyrimidine No. 357. 2-4'-(2'''-Fluoro-4''methylpentoxy)phenyl-5-(4'-nonylphenyl)-pyrimidine No. 358. 2-4'-(2'''-Fluoro-4''methylpentoxy)phenyl-5-(4'-decylphenyl)-pyrimidine No. 359. 2-4'-(2'''-Fluoro-4''methylpentoxy)phenyl-5-(4'-undecylphenyl)-pyrimidine No. 360. 2-4'-(2'''-Fluoro-4''methylpentoxy)phenyl-5-(4'-dodecylphenyl)-pyrimidine No. 361. 2-4'-(2'''-Fluoropropoxy)phenyl-5-(4'-butoxyphenyl)-pyrimidine No. 362. 2-4'-(2'''-Fluoropropoxy)phenyl-5-(4'-pentoxyphenyl)-pyrimidine No. 363. 2-4'-(2'''-Fluoropropoxy)phenyl-5-(4'-hexyloxyphenyl)-pyrimidine No. 364. 2-4'-(2'''-Fluoropropoxy)phenyl-5-(4'-heptyloxyphenyl)-pyrimidine No. 365. 2-4'-(2'''-Fluoropropoxy)phenyl-5-(4'-octyloxyphenyl)-pyrimidine No. 366. 2-4'-(2'''-Fluoropropoxy)phenyl-5-(4'-nonyoxylphenyl)-pyrimidine No. 367. 2-4'-(2'''-Fluoropropoxy)phenyl-5-(4'-decyloxyphenyl)-pyrimidine No. 368. 2-4'-(2'''-Fluoropropoxy)phenyl-5-(4'-undecyloxyphenyl)-pyrimidine No. 369. 2-4'-(2'''-Fluoropropoxy)phenyl-5-(4'-dodecyloxyphenyl)-pyrimidine No. 370. 2-4'-(2'''-Fluorobutoxy)phenyl-5-(4'-butoxyphenyl)-pyrimidine No. 371. 2-4'-(2'''-Fluorobutoxy)phenyl-5-(4'-pentoxyphenyl)-pyrimidine No. 372. 2-4'-(2'''-Fluorobutoxy)phenyl-5-(4'-hexyloxyphenyl)-pyrimidine No. 373. 2-4'-(2'''-Fluorobutoxy)phenyl-5-(4'-heptyloxyphenyl)-pyrimidine No. 374. 2-4'-(2'''-Fluorobutoxy)phenyl-5-(4'-octyloxyphenyl)-pyrimidine No. 375. 2-4'-(2'''-Fluorobutoxy)phenyl-5-(4'-nonyoxylphenyl)-pyrimidine No. 376. 2-4'-(2'''-Fluorobutoxy)phenyl-5-(4'-decyloxyphenyl)-pyrimidine No. 377. 2-4'-(2'''-Fluorobutoxy)phenyl-5-(4'-undecyloxyphenyl)-pyrimidine No. 378. 2-4'-(2'''-Fluorobutoxy)phenyl-5-(4'-dodecyloxyphenyl)-pyrimidine No. 379. 2-4'-(2'''-Fluoropentoxy)phenyl-5-(4'-butoxyphenyl)-pyrimidine No. 380. 2-4'-(2'''-Fluoropentoxy)phenyl-5-(4'-pentoxyphenyl)-pyrimidine No. 381. 2-4'-(2'''-Fluoropentoxy)phenyl-5-(4'-hexyloxyphenyl)-pyrimidine No. 382. 2-4'-(2'''-Fluoropentoxy)phenyl-5-(4'-heptyloxyphenyl)-pyrimidine No. 383. 2-4'-(2'''-Fluoropentoxy)phenyl-5-(4'-octyloxyphenyl)-pyrimidine No. 384. 2-4'-(2'''-Fluoropentoxy)phenyl-5-(4'-nonyoxylphenyl)-pyrimidine No. 385. 2-4'-(2'''-Fluoropentoxy)phenyl-5-(4'-decyloxyphenyl)-pyrimidine No. 386. 2-4'-(2'''-Fluoropentoxy)phenyl-5-(4'-undecyloxyphenyl)-pyrimidine No. 387. 2-4'-(2'''-Fluoropentoxy)phenyl-5-(4'-dodecyloxyphenyl)-pyrimidine No. 388. 2-4'-(2'''-Fluorohexyloxy)phenyl-5-(4'-butoxyphenyl)-pyrimidine No. 389. 2-4'-(2'''-Fluorohexyloxy)phenyl-5-(4'-pentoxyphenyl)-pyrimidine No. 390. 2-4'-(2'''-Fluorohexyloxy)phenyl-5-(4'-hexyloxyphenyl)-pyrimidine No. 391. 2-4'-(2'''-Fluorohexyloxy)phenyl-5-(4'-heptyloxyphenyl)-pyrimidine No. 392. 2-4'-(2'''-Fluorohexyloxy)phenyl-5-(4'-octyloxyphenyl)-pyrimidine No. 393. 2-4'-(2'''-Fluorohexyloxy)phenyl-5-(4'-nonyoxylphenyl)-pyrimidine No. 394. 2-4'-(2'''-Fluorohexyloxy)phenyl-5-(4'-decyloxyphenyl)-pyrimidine No. 395. 2-4'-(2'''-Fluorohexyloxy)phenyl-5-(4'-undecyloxyphenyl)-pyrimidine No. 396. 2-4'-(2'''-Fluorohexyloxy)phenyl-5-(4'-dodecyloxyphenyl)-pyrimidine No. 397. 2-4'-(2'''-Fluoroheptyloxy)phenyl-5-(4'-butoxyphenyl)-pyrimidine No. 398. 2-4'-(2'''-Fluoroheptyloxy)phenyl-5-(4'-pentoxyphenyl)-pyrimidine No. 399. 2-4'-(2'''-Fluoroheptyloxy)phenyl-5-(4'-hexyloxyphenyl)-pyrimidine No. 400. 2-4'-(2'''-Fluoroheptyloxy)phenyl-5-(4'-heptyloxyphenyl)-pyrimidine No. 401. 2-4'-(2'''-Fluoroheptyloxy)phenyl-5-(4'-octyloxyphenyl)-pyrimidine No. 402. 2-4'-(2'''-Fluoroheptyloxy)phenyl-5-(4'-nonyoxylphenyl)-pyrimidine No. 403. 2-4'-(2'''-Fluoroheptyloxy)phenyl-5-(4'-decyloxyphenyl)-pyrimidine No. 404. 2-4'-(2'''-Fluoroheptyloxy)phenyl-5-(4'-undecyloxyphenyl)-pyrimidine No. 405. 2-4'-(2'''-Fluoroheptyloxy)phenyl-5-(4'-dodecyloxyphenyl)-pyrimidine No. 406. 2-4'-(2'''-Fluorooctyloxy)phenyl-5-(4'-butoxyphenyl)-pyrimidine No. 407. 2-4'-(2'''-Fluorooctyloxy)phenyl-5-(4'-pentoxyphenyl)-pyrimidine No. 408. 2-4'-(2'''-Fluorooctyloxy)phenyl-5-(4'-hexyloxyphenyl)-pyrimidine No. 409. 2-4'-(2'''-Fluorooctyloxy)phenyl-5-(4'-heptyloxyphenyl)-pyrimidine No. 410. 2-4'-(2'''-Fluorooctyloxy)phenyl-5-(4'-octyloxyphenyl)-pyrimidine No. 411. 2-4'-(2'''-Fluorooctyloxy)phenyl-5-(4'-nonyoxylphenyl)-pyrimidine No. 412. 2-4'-(2'''-Fluorooctyloxy)phenyl-5-(4'-decyloxyphenyl)-pyrimidine No. 413. 2-4'-(2'''-Fluorooctyloxy)phenyl-5-(4'-undecyloxyphenyl)-pyrimidine No. 414. 2-4'-(2'''-Fluorooctyloxy)phenyl-5-(4'-dodecyloxyphenyl)-pyrimidine No. 415. 2-4'-(2'''-Fluorononyloxy)phenyl-5-(4'-butoxyphenyl)-pyrimidine No. 416. 2-4'-(2'''-Fluorononyloxy)phenyl-5-(4'-pentoxyphenyl)-pyrimidine No. 417. 2-4'-(2'''-Fluorononyloxy)phenyl-5-(4'-hexyloxyphenyl)-pyrimidine No. 418. 2-4'-(2'''-Fluorononyloxy)phenyl-5-(4'-heptyloxyphenyl)-pyrimidine No. 419. 2-4'-(2'''-Fluorononyloxy)phenyl-5-(4'-octyloxyphenyl)-pyrimidine No. 420. 2-4'-(2'''-Fluorononyloxy)phenyl-5-(4'-nonyoxylphenyl)-pyrimidine No. 421. 2-4'-(2'''-Fluorononyloxy)phenyl-5-(4'-decyloxyphenyl)-pyrimidine No. 422. 2-4'-(2'''-Fluorononyloxy)phenyl-5-(4'-undecyloxyphenyl)-pyrimidine No. 423. 2-4'-(2'''-Fluorononyloxy)phenyl-5-(4'-dodecyloxyphenyl)-pyrimidine No. 424. 2-4'-(2'''-Fluorodecyloxy)phenyl-5-(4'-butoxyphenyl)-pyrimidine No. 425. 2-4'-(2''-Fluorodecyloxy)phenyl-5-(4'-pentoxyphenyl)-pyrimidine
No. 426. 2-4'-(2''-Fluorodecyloxy)phenyl-5-(4'-hexyloxyphenyl)-pyrimidine
No. 427. 2-4'-(2''-Fluorodecyloxy)phenyl-5-(4'-heptyloxyphenyl)-pyrimidine
No. 428. 2-4'-(2''-Fluorodecyloxy)phenyl-5-(4'-octyloxyphenyl)-pyrimidine
No. 429. 2-4'-(2''-Fluorodecyloxy)phenyl-5-(4'-nonyoxylphenyl)-pyrimidine
No. 430. 2-4'-(2''-Fluorodecyloxy)phenyl-5-(4'-decyloxyphenyl)-pyrimidine
No. 431. 2-4'-(2''-Fluorodecyloxy)phenyl-5-(4'-undecyloxyphenyl)-pyrimidine
No. 432. 2-4'-(2''-Fluorodecyloxy)phenyl-5-(4'-dodecyloxyphenyl)-pyrimidine
No. 433. 2-4'-(2''-Fluoroundecyloxy)phenyl-5-(4'-butoxyphenyl)-pyrimidine
No. 434. 2-4'-(2''-Fluoroundecyloxy)phenyl-5-(4'-pentoxyphenyl)-pyrimidine
No. 435. 2-4'-(2''-Fluoroundecyloxy)phenyl-5-(4'-hexyloxyphenyl)-pyrimidine
No. 436. 2-4'-(2''-Fluoroundecyloxy)phenyl-5-(4'-heptyloxyphenyl)-pyrimidine
No. 437. 2-4'-(2''-Fluoroundecyloxy)phenyl-5-(4'-octyloxyphenyl)-pyrimidine
No. 438. 2-4'-(2''-Fluoroundecyloxy)phenyl-5-(4'-nonyoxylphenyl)-pyrimidine
No. 439. 2-4'-(2''-Fluoroundecyloxy)phenyl-5-(4'-decyloxyphenyl)-pyrimidine
No. 440. 2-4'-(2''-Fluoroundecyloxy)phenyl-5-(4'-undecyloxyphenyl)-pyrimidine
No. 441. 2-4'-(2''-Fluoroundecyloxy)phenyl-5-(4'-dodecyloxyphenyl)-pyrimidine
No. 442. 2-4'-(2''-Fluorododecyloxy)phenyl-5-(4'-butoxyphenyl)-pyrimidine
No. 443. 2-4'-(2''-Fluorododecyloxy)phenyl-5-(4'-pentoxyphenyl)-pyrimidine
No. 444. 2-4'-(2''-Fluorododecyloxy)phenyl-5-(4'-hexyloxyphenyl)-pyrimidine
No. 445. 2-4'-(2''-Fluorododecyloxy)phenyl-5-(4'-heptyloxyphenyl)-pyrimidine
No. 446. 2-4'-(2''-Fluorododecyloxy)phenyl-5-(4'-octyloxyphenyl)-pyrimidine
No. 447. 2-4'-(2''-Fluorododecyloxy)phenyl-5-(4'-nonyoxylphenyl)-pyrimidine
No. 448. 2-4'-(2''-Fluorododecyloxy)phenyl-5-(4'-decyloxyphenyl)-pyrimidine
No. 449. 2-4'-(2''-Fluorododecyloxy)phenyl-5-(4'-undecyloxyphenyl)-pyrimidine
No. 450. 2-4'-(2''-Fluorododecyloxy)phenyl-5-(4'-dodecyloxyphenyl)-pyrimidine
No. 451. 2-4'-(2''-Fluoro-3''-methylbutoxy)phenyl-5-(4'-butoxyphenyl)-pyrimidine
No. 452. 2-4'-(2''-Fluoro-3''-methylbutoxy)phenyl-5-(4'-pentoxyphenyl)-pyrimidine
No. 453. 2-4'-(2''-Fluoro-3''-methylbutoxy)phenyl-5-(4'-hexyloxyphenyl)-pyrimidine
No. 454. 2-4'-(2''-Fluoro-3''-methylbutoxy)phenyl-5-(4'-heptyloxyphenyl)-pyrimidine
No. 455. 2-4'-(2''-Fluoro-3''-methylbutoxy)phenyl-5-(4'-octyloxyphenyl)-pyrimidine
No. 456. 2-4'-(2''-Fluoro-3''-methylbutoxy)phenyl-5-(4'-nonyloxyphenyl)-pyrimidine
No. 457. 2-4'-(2''-Fluoro-3''-methylbutoxy)phenyl-5-(4'-decyloxyphenyl)-pyrimidine
No. 458. 2-4'-(2''-Fluoro-3''-methylbutoxy)phenyl-5-(4'-undecyloxyphenyl)-pyrimidine
No. 459. 2-4'-(2''-Fluoro-3''-methylbutoxy)phenyl-5-(4'-dodecyloxyphenyl)-pyrimidine
No. 460. 2-4'-(2''-Fluoro-3''-methylpentoxy)phenyl-5-(4'-butoxyphenyl)-pyrimidine
No. 461. 2-4'-(2''-Fluoro-3''-methylpentoxy)phenyl-5-(4'-pentoxyphenyl)-pyrimidine
No. 462. 2-4'-(2''-Fluoro-3''-methylpentoxy)phenyl-5-(4'-hexyloxyphenyl)-pyrimidine
No. 463. 2-4'-(2''-Fluoro-3''-methylpentoxy)phenyl-5-(4'-heptyloxyphenyl)-pyrimidine
No. 464. 2-4'-(2''-Fluoro-3''-methylpentoxy)phenyl-5-(4'-octyloxyphenyl)-pyrimidine
No. 465. 2-4'-(2''-Fluoro-3''-methylpentoxy)phenyl-5-(4'-nonyloxyphenyl)-pyrimidine
No. 466. 2-4'-(2''-Fluoro-3''-methylpentoxy)phenyl-5-(4'-decyloxyphenyl)-pyrimidine
No. 467. 2-4'-(2''-Fluoro-3''-methylpentoxy)phenyl-5-(4'-undecyloxyphenyl)-pyrimidine
No. 468. 2-4'-(2''-Fluoro-3''-methylpentoxy)phenyl-5-(4'-dodecyloxyphenyl)-pyrimidine
No. 469. 2-4'-(2''-Fluoro-4''-methylpentoxy)phenyl-5-(4'-butoxyphenyl)-pyrimidine
No. 470. 2-4'-(2''-Fluoro-4''-methylpentoxy)phenyl-5-(4'-pentoxyphenyl)-pyrimidine
No. 471. 2-4'-(2''-Fluoro-4''-methylpentoxy)phenyl-5-(4'-hexyloxyphenyl)-pyrimidine
No. 472. 2-4'-(2''-Fluoro-4''-methylpentoxy)phenyl-5-(4'-heptyloxyphenyl)-pyrimidine
No. 473. 2-4'-(2''-Fluoro-4''-methylpentoxy)phenyl-5-(4'-octyloxyphenyl)-pyrimidine
No. 474. 2-4'-(2''-Fluoro-4''-methylpentoxy)phenyl-5-(4'-nonyloxyphenyl)-pyrimidine
No. 475. 2-4'-(2''-Fluoro-4''-methylpentoxy)phenyl-5-(4'-decyloxyphenyl)-pyrimidine
No. 476. 2-4'-(2''-Fluoro-4''-methylpentoxy)phenyl-5-(4'-undecyloxyphenyl)-pyrimidine
No. 477. 2-4'-(2''-Fluoro-4''-methylpentoxy)phenyl-5-(4'-dodecyloxyphenyl)-pyrimidine In the present invention, the single compound or the composition used as the constituent of ferroelectric liquid crystals is characterized by a very quick response. The reason is that the compounds of the present invention have a high value of spontaneous polarization, as the result of which a quick response can be realized. As shown in the examples described hereinafter, the compound which has a ferroelectric liquid crystal phase by itself shows a very quick response. For example, a quick response of 4–10 msec is realized as shown in Example 3. Not only the compound having a ferroelectric liquid crystal phase by itself, but also the compound not having the said phase can realize a very quick response, when these compounds are used as constituents of ferroelectric liquid crystals.

Furthermore, the compounds of the present invention can easily have liquid crystal phases. The compounds described in Japanese Patent Application No. 62-262819 have a high value of $P_S$, but it is difficult to show liquid crystalization. For this reason, when these compounds are used as a constituent of a ferroelectric liquid crystal composition, the quantity to be used is limited. On the other hand, the compounds of the present invention have a high value of $P_S$, and it is easy to have the ferroelectric liquid crystal phases, so that the quantity is not limited when these compounds are used as a constituent of the liquid crystal composition.

As the compounds of the present invention have asymmetric carbon atoms, they can induce twisted structure by adding them to nematic liquid crystals. As the nematic liquid crystals having the twisted structure, namely chiral nematic liquid crystals, do not form so-called reverse twist domain of the TN type display element, the crystals can be used as an inhibitor of the reverse domain formation.

Furthermore, many chiral nematic liquid crystal compositions obtained by the addition of the compounds of the present invention to the nematic liquid crystal composition have negative temperature characteristics of the chiral pitch as exemplified below by Examples later. The chiral pitch of most chiral materials for addition to nematic liquid crystals becomes longer as the temperature rises. However, there are reports of materials of which the chiral pitch becomes shorter as the temperature rises, and the threshold voltage of electro-optic characteristics of the TN type display element varies slightly with temperature. (Ref., Lecture Collection of 33th Combined Meeting of Applied Physics Field, 1P-G-7, page 78, spring 1986, and Lecture Collection of JAPAN DISPLAY, 8.3, page 286–289, 1986.)

As the compounds of the present invention have physical properties similar to the properties of the above compounds, the chiral nematic liquid crystal composition of which the threshold voltage varies slightly with temperature can be obtained by adding the compounds of the present invention.

Otherwise, in so-called super TN type display having a twist angle 180–270 degrees, marked lowering of display quality is brought about by changes of pitch with temperature. However, by using the chiral nematic liquid crystal composition which is obtained by adding the compound of the present invention, excellent super TN type display elements in which the display quality is not spoiled by the temperature changes can be made.

As described above, the compounds of the present invention are useful as the compounds of chiral ingredients of chiral nematic compositions.

The production method of the compounds of the present invention is described hereinafter.

A method for preparing compound (I) of the present invention preferably includes the following process.

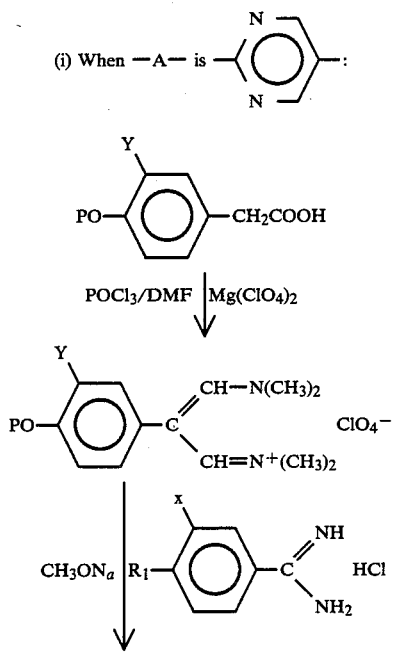

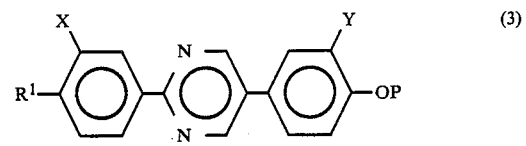

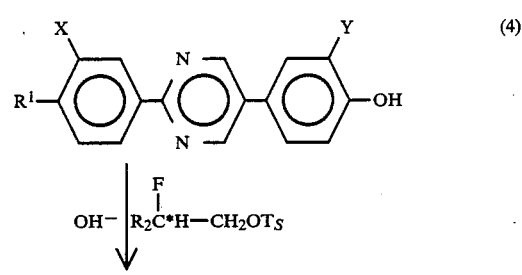

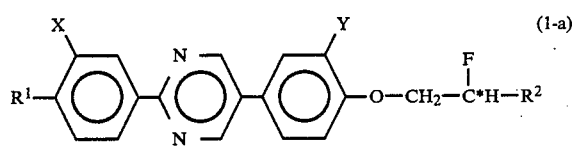

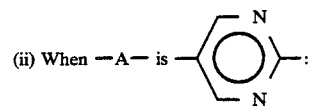

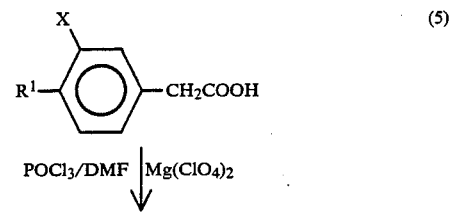

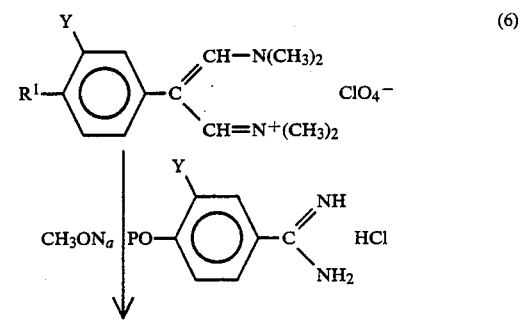

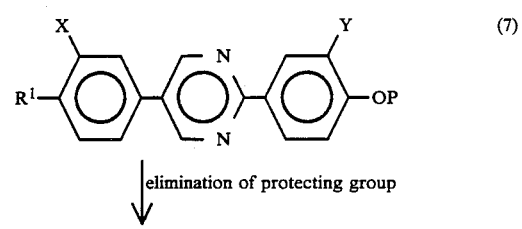

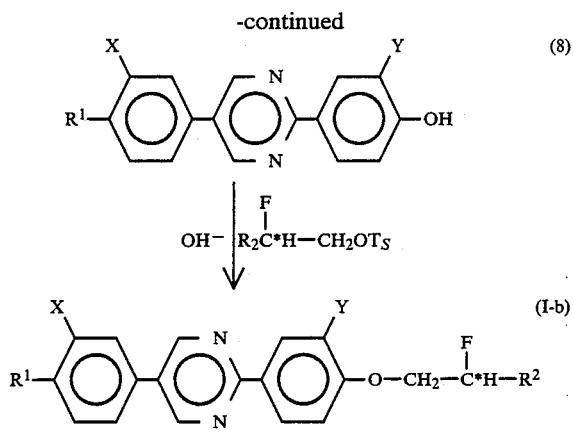

wherein $R^1$, $R^2$, X and Y have the same meanings as described above, and P shows a suitable protecting group.

Namely, compounds (2) and (6) are obtained by reacting substituted phenyl acetic acids (1) and (5) with phosphorus oxychloride, dimethylformamide and then magnesium perchlorate. Compounds (3) and (7) are obtained by reacting the compounds (2) and (6) with substituted benzamidine hydrochloride under basic conditions. After compounds (4) and (8) are obtained by eliminating protecting groups of compounds (3) and (7), objective compounds (I-a) and (I-b) are obtained by reacting compounds (4) and (8) with optically active fluoro alkyl toluenesulfonate, respectively.

Furthermore, this optically active fluoro alkyl toluenesulfonate can be prepared by the following process. For example, the optically active fluoro alcohol is obtained by a method, e.g., ring-opening of an optically active epoxy alkane by using HF-pyridine complex reagent, diazohzing of an amino acid by using HF-pyridine complex reagent and the like. This alcohol is reacted with p-toluenesulfonyl chloride to obtain the above optically active fluoro alkyl toluenesulfonate.

According to the compounds of the present invention, any compounds can be used as components of ferroelectric liquid crystal compositions. These compounds having substantially high values of spontaneous polarization are applicable to liquid crystal materials, especially display materials showing a quick response.

Furthermore, when the compounds of the present invention are used as components of liquid crystal compositions, the compounds are very useful ferroelectric liquid crystal materials showing perferable temperature regions of ferroelectric liquid crystals. Chiral nematic liquid crystal compositions obtained by adding the compounds of the present invention to nematic liquid crystal compositions are useful as inhibitors of reverse twist domain production and small change of threshold voltage can be obtained.

Therefore, excellent super TN type display elements which do not degrade by due to temperature changes can be obtained.

DESCRIPTION OF THE PREFERRED EMBODIMENTS

The following examples illustrate the present invention more specifically.

EXAMPLE 1

Production of (S)-2-(4'-nonylphenyl)-5-4'-(2''-fluorooctyloxy)phenylpyrimidine (No. 60) wherein $R^1$ indicates

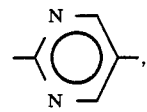

1st Step

Production of 2-(4'-nonylphenyl)-5-(4'-methoxyphenyl)pyrimidine (In the formula (3), $R^1$ is nonyl, X=Y=H, and P=$CH_3$)

After 184 g of phosphorus oxychloride was added dropwise to 146 g of dimethylformamide at 0° C., 66 g of p-methoxyphenyl acetate was added little by little to the mixture at −10° C. The mixture was stirred at 20° C. for one hour, at 60° C. for two hours and at 80° C. for five hours. Dimethylformamide was distilled away under vacuum, and the residue was cooled and added to a solution saturated with magnesium perchlorate. The obtained crystals were separated by filtration and washed with ether. A salt of 67 g was obtained and its melting points was 133.3°–134.4° C.

A mixture of 60 g of the salt, 48 g of p-nonyl benzamidine hydrochloride, 13.6 g of sodium methoxide and 600 ml of ethanol was refluxed for six hours. Toluene was added to the mixture. The mixture was washed with alkali solution and then with water. The solvent was distilled away. Recrystallization of the residue by using a mixture of ethanol and ethyl acetate gave 60 g of 5-(4-methoxyphenyl)-2-(4-nonylphenyl)pyrimidine.

This compound showed liquid crystal property and its phase transition temperatures were as follows.

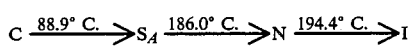

2nd Step

Production of 2(4'-nonylphenyl)-5-(4'-hydroxyphenyl)pyrimidine (In the formula (4), $R^1$ is nonyl and X=Y=H)

A mixture of 60 g of 2-(4'-nonylphenyl)-5-(4'-methoxyphenyl)pyrimidine, 240 g of hydrobromic acid and one liter of acetic acid was refluxed for 40 hours. After a large portion of acetic acid was distilled away, the residue was added to a solution of 2N sodium hydroxide. The obtained crystals were recrystallized from ethyl acetate, and 32.6 g of 2-(4'-nonylphenyl)-5-(4'-hydroxyphenyl)pyrimidine was obtained. This compound showed liquid crystal property and its phase transition temperatures were 98.4° C. at C-$S_A$ phase and 138.6° C. at $S_A$-I phase.

3rd Step

Production of (S)-2-fluoro-1-p-toluenesulfonyloxyoctane

To 30 ml of hydrogen fluoride pyridine solution which was cooled with ice, 8.5 g of (R)-1,2-epoxyoctane in 20 ml of ether was added dropwise. The mixture was stirred for one hour at the same temperature and brought to room temperature. 100 ml of water was added to the mixture. After extracting it with 50 ml of ether twice, the obtained organic layer was washed with an alkali solution and then with water, dried over magnesium sulfate and concentrated. The concentrate was distilled under reduced pressure and 4.9 g of distillate was obtained at 126°–129° C./80 mmHg. 3.7 g of (S)-2-fluorooctane-1-ol was obtained by recrystallization from 40 ml of heptane. Its melting point was 33°–35° C., $[\alpha]_D^{26} -13.14$ (c1.7, benzene) of optical rotation was shown.

Three grams of the obtained (S)-2-fluorooctane-1-ol, 4.5 g of p-toluenesulfonyl chloride and 50 ml of pyridine were stirred at room temperature. 100 ml of water and 200 ml of toluene were added to the solution. The organic layer was separated and washed with an acid solution, with an alkali solution and with water, dried over magnesium sulfate, and concentrated. 6.0 g of (S)-2-fluoro-1-p-toluenesulfonyloxyoctane was obtained.

4th Step

Production of the title compound

A mixture of 80 mg of hydrogenated sodium, 10 mg of tetrahydrofuran, 360 mg of 2-(4'-nonylphenyl)-5-(4'-hydroxyphenyl)pyrimidine, 350 mg of (S)-2-fluoro-1-p-toluenesulfonyloxyoctane and 50 ml of dimethyformamide was stirred at temperature of about 70° C. for eight hours. 150 ml of toluene was added to the solution. The separated organic layer was washed with an alkali solution and with water, and concentrated. The obtained concentrate was subjected to column chromatography on silica gel by using a toluene solution for eluting. The purified compound was recrystallized with ethanol. 180 mg of the title compound, (S)-2-(4'-nonylphenyl)-5-4'-(2"-fluorooctyloxy)phenyl pyrimidine was obtained. The phase transition temperatures of the above compound were shown as follows.

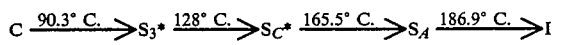

wherein $S_3^*$ is a ferroelectric liquid crystal phase, type of which is unknown.

EXAMPLE 2

Production of (S)-2-4'-(2"-fluorooctyloxy)phenyl-5-(4'-butylphenyl)pyrimidine (No. 289)(In the formula (1),

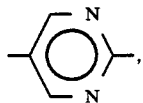

A mixture of 100 mg of hydrogenated sodium, 15 ml of tetrahydrofuran, 300 mg of 2-(4'-hydroxyphenyl)-5-(4'-butylphenyl)pyrimidine, 350 mg of (S)-2-fluoro-1-p-toluenesulfonyloxyoctane and 60 mg of dimethylformamide was stirred at temperature of about 70° C. for eight hours. 200 ml of toluene was added to the solution. The separated organic layer was washed with an alkali solution and with water, and concentrated. The obtained concentrate was subjected to column chromatography on silica gel by using an eluting toluene solution.

The purified compound was recrystallized with ethanol. 170 mg of the title compound, (S)-2-4'-(2"-fluorooctyloxy)phenyl-5-(4'-butylphenyl)pyrimidine was obtained. The phase transition temperatures of the above compound were shown as follows.

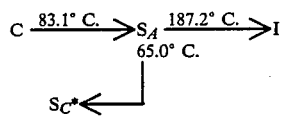

EXAMPLE 3 (Using Example 1)

2-(4'-nonylphenyl)-5-4'-(2"-fluorooctyloxy)phenylpyrimidine was injected into a cell 2 μm in thickness having transparent electrodes obtained by homogeneous aligning treatment. The treatment was conducted by the application of polyvinylalcohol as an aligning agent to the surfaces of the electrodes and rubbing the applied surfaces. The resulting element of liquid crystals was placed between two polarizers which intersected each other. ±10 V was applied to the element. The change of transmittance of light was observed. The response time of the element which was determined by the intensity change of transmittance of light and $P_S$ of the spontaneous polarization which was determined by Sawyer-Tower method were shown as follows.

| Temperature (°C.) | Response time (μ sec) | $P_S$ (nC/cm$^2$) |
| --- | --- | --- |
| 161.5 | 4 | 32.3 |
| 156.5 | 6 | 44.0 |
| 146.5 | 7 | 63.6 |
| 136.5 | 10 | 82.4 |

The compounds of the present invention as described above which showed the ferroelectric liquid crysral phases by themselves have great $P_S$ and short response time.

EXAMPLE 4 (Use Example 2)

Firstly, a composition was prepared by using the following liquid crystal compounds.

n-C$_6$H$_{13}$O—〇—〇—C$_8$H$_{17}$    30 wt % n-C$_8$H$_{17}$O—〇—〇—C$_8$H$_{17}$    20 wt % n-C$_9$H$_{19}$O—〇—〇—C$_8$H$_{17}$    10 wt % n-C$_{10}$H$_{21}$O—〇—〇—C$_8$H$_{17}$    10 wt % n-C$_6$H$_{13}$—〇—〇—〇—C$_8$H$_{17}$    20 wt %

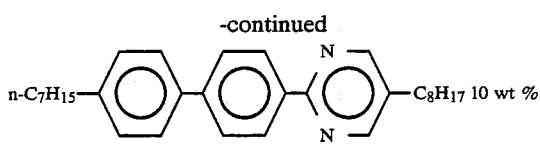

The phase transition temperatures of the above composition A were shown as the following:

As the composition merely contains nonoptical active compounds, it is not a chiral liquid crystal composition. Accordingly, the composition does not have the spontaneous polarization.

A mixture of 80% by weight of composition A and 20% by weight of (S)-2-[4'-(2''-fluorooctyloxy)phenyl]-5-(4'-butylphenyl)pyrimidine of the present invention, namely composition B shows ferroelectric $S_C^*$ phase at room temperature, and the phase transition temperatures were as follows:

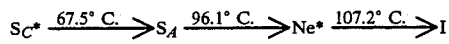

The response times and $P_S$ of this composition B under the same conditions as described in Example 3 (Use Example 1) were shown as follows.

| Temperature (°C.) | Response time (μ sec) | $P_S$ (nC/cm$^2$) |
|---|---|---|
| 57.5 | 37 | 8.6 |
| 40 | 86 | 15.0 |
| 30 | 180 | 17.4 |

As shown above, by using the compound (I) of the present invention, $P_S$ can be added to the nonchiral smectic composition, and the ferroelectric liquid crystal composition which shows short response time at room temperature is obtained.

EXAMPLE 5 (Use Example 3)

A nematic liquid crystal composition containing the following compounds:

C$_2$H$_5$—〇—〇—CN  20 wt % n-C$_5$H$_{11}$—〇—〇—CN  35 wt % n-C$_8$H$_{17}$O—〇—〇—CN  30 wt % n-C$_5$H$_{11}$—〇—〇—〇—CN  15 wt % was injected into a cell having electrodes at an interval of 10 μm. The cell was treated by the application of polyvinylalcohol as an aligning agent to the surfaces of the electrodes and rubbing the applied surfaces. The resulting TN type cell was observed under a polarization microscope, and it was found that reverse twist domain was produced.

To the above nematic liquid crystal composition, two percent by weight of the compound obtained by Example 2, namely (S)-2-[4'-(2''-fluorooctyloxy)phenyl]-5-(4'-butylphenyl)pyrimidine was added. The TN type cell obtained by the same method as described above was observed under the polarization microscope. The reverse twist domain was dissolved, and a homogeneous nematic phase was observed.

EXAMPLE 6 (Use Example 4)

By adding 1% by weight of the compound obtained by Example 1, namely (S)-2-(4'-nonylphenyl)-5-[4'-(2''-fluorooctyloxy)phenyl]pyrimidine to a nematic liquid crystal composition ZLI 1132 prepared by Merck & Co. Inc., a chiral nematic liquid crystal composition was prepared. The chiral pitch of the obtained composition was determined by Canor-wedge method (Applied Physics 43 (2), 126–131, 1974) and negative temperature characteristics were shown as follows.

| Temperature (°C.) | Pitch length (μm) |
|---|---|
| 20 | 71.1 |
| 30 | 66.0 |
| 40 | 60.2 |
| 50 | 55.4 |
| 60 | 52.0 |
| 70 | 49.3 |

We claim:

1. A fluoroalkoxydiphenyl pyrimidine represented by the following formula:

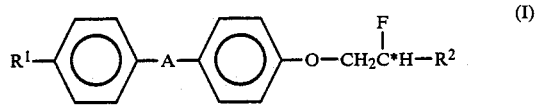

wherein R$^1$ is alkyl or alkoxy of 4–9 carbon atoms, R$^2$ is alkyl of 5–8 carbon atoms, —A— is

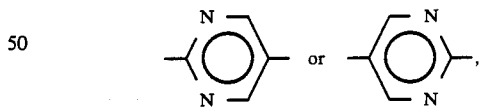

and * indicates that its carbon atom is an asymmetric carbon atom.

2. A liquid crystal composition containing at least two components, at least one of which is a fluoroalkoxydiphenyl pyrimidine represented by the following formula:

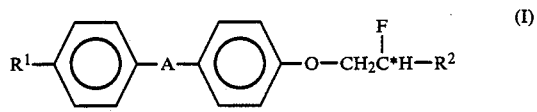

wherein R$^1$ is alkyl or alkoxy of 4–9 carbon atoms, R$^2$ is alkyl of 5–8 carbon atoms, —A— is

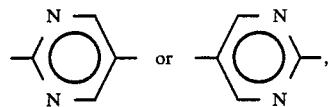

and * indicates that its carbon atom is an asymmetric carbon atom.

3. The liquid crystal composition as claimed in claim 2, wherein the presented liquid phase is a chiral smectic phase.

4. The liquid crystal composition as claimed in claim 2, wherein the presented liquid phase is a chiral nematic phase.

5. An electro-optic element containing a liquid crystal composition which comprises at least one fluoroalkoxydiphenyl pyrimidine represented by the following formula:

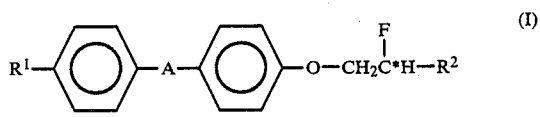

wherein $R^1$ is alkyl or alkoxy of 4–9 carbon atoms, $R^2$ is alkyl of 5–8 carbon atoms, —A— is

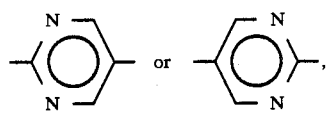

and * indicates that its carbon atom is an asymmetric carbon atom.

* * * * *